US008298190B2

(12) United States Patent
House

(10) Patent No.: US 8,298,190 B2
(45) Date of Patent: Oct. 30, 2012

(54) DEVICES AND METHODS FOR SECURING CATHETER ASSEMBLIES

(75) Inventor: Jamie Glen House, Colorado Springs, CO (US)

(73) Assignee: Adapta Medical, Inc., Colorado Springs, CO (US)

( * ) Notice: Subject to any disclaimer, the term of this patent is extended or adjusted under 35 U.S.C. 154(b) by 0 days.

(21) Appl. No.: 13/104,452

(22) Filed: May 10, 2011

(65) Prior Publication Data

US 2011/0213345 A1   Sep. 1, 2011

Related U.S. Application Data

(63) Continuation of application No. 11/652,523, filed on Jan. 12, 2007, now Pat. No. 7,938,807.

(51) Int. Cl.
*A61M 5/32* (2006.01)
*A61M 27/00* (2006.01)

(52) U.S. Cl. ........ 604/180; 604/544; 604/177; 604/174; 604/171

(58) Field of Classification Search .................. 604/174, 604/177–180, 605, 544, 905, 171
See application file for complete search history.

(56) References Cited

U.S. PATENT DOCUMENTS

| | | | | | |
|---|---|---|---|---|---|
| 3,288,136 | A | * | 11/1966 | Lund | 604/180 |
| 4,652,259 | A | * | 3/1987 | O'Neil | 604/544 |
| 5,192,273 | A | * | 3/1993 | Bierman | 604/174 |
| 2001/0011164 | A1 | * | 8/2001 | Bierman | 604/180 |

* cited by examiner

*Primary Examiner* — Nicholas Lucchesi
*Assistant Examiner* — Leah Stohr
(74) *Attorney, Agent, or Firm* — Moazzam & Associates, LLC

(57) ABSTRACT

A connecting device for a catheter assembly is disclosed allowing a user to connect a catheter assembly to an adhesive pad which is then capable of anchoring the catheter assembly to a patient's leg. The connecting device may have an introducer body with an extension body and an attachment mechanism. The connecting device can be rotated along with or within a collar in a circular manner in order to facilitate the making of the connection with the adhesive pad. Additionally, the connecting device may contain an enlarged portion to enhance operability.

13 Claims, 3 Drawing Sheets

DEVICES AND METHODS FOR SECURING CATHETER ASSEMBLIES

This application is a continuation of U.S. patent application Ser. No. 11/652,523, filed Jan. 12, 2007, now U.S. Pat. No. 7,938,807, the content of which is hereby incorporated by reference in its entirety into this disclosure.

BACKGROUND OF THE INVENTION

1. Field of the Invention

The present invention relates generally to catheter assemblies. More particularly, the present invention relates to catheter assemblies and devices having attachment mechanisms.

2. Background of the Invention

The urinary catheterization procedure is a common medical practice with the procedure being performed today in hospitals, nursing homes, and home settings. When a patient requires a catheter to remain in for a prolonged period of time, an indwelling or Foley catheter is often used. This type of catheter has the benefit of remaining in the bladder for up to one month, which decreases the inconvenience of repeated intermittent catheterization. Indwelling urinary catheters are also used in situations where an accurate measurement of urine is required.

One common difficulty with indwelling catheters is the mobility of the collection bag. The bedside collection bags are usually of a standard size and can hold up to 2000 mL of urine. The indwelling urinary catheter often comes connected to the bedside collection bag to create a "closed system" environment.

Conventional urine collection bags have a drain port located somewhere on the bag. Several times throughout the day the nurse or caretaker is required to open the port and drain the urine into a container for discard. Yet, many times in the hospital setting the patient must get out of bed and walk to the bathroom or shower, or the patient must get out of bed for therapy or exercise with the bag attached. Even If a smaller bag is used (e.g., initially or it is switched before the patient gets up), the patient or caretaker must tend the collection bag while avoiding physical contact during the walk or exercise. This can be very inconvenient and hazardous.

Because it is inconvenient for a patient or caretaker to tend a collection bag while the patient is mobile, there is a need in the healthcare industry for a sterile and convenient technique for facilitating the catheterization process and allowing for a more convenient technique for securing or transporting an in-use collection bag.

SUMMARY OF THE INVENTION

The current techniques for catheterization are inefficient and inconvenient. It is inconvenient and unsafe for a patient or caretaker to tend a collection bag when the patient is mobile. The present invention addresses this healthcare problem and other related to it by providing various devices and techniques to facilitate the catheterization process, and to allow for easier transport of an in-use collection bag. More specifically, the present invention proposes an introducer connected to a proximal end of a catheter assembly wherein the introducer possesses an attachment mechanism capable of mating with a corresponding pad attachment mechanism on an adhesive pad. Thus, the present invention allows an adhesive pad to be conveniently connected to the catheter assembly for increased patient mobility.

In one exemplary embodiment, the present invention is a connecting device for a catheter assembly. The device includes an introducer body having an attachment mechanism on its surface wherein the introducer body can be translated along the length of a catheter.

In another exemplary embodiment, the present invention is a connecting device for a catheter assembly. The device includes an introducer body, including an extension body and an enlarged portion with an attachment mechanism on its surface; and wherein the introducer body can be translated along the length of a catheter.

In yet another exemplary embodiment, the present invention is a connecting device for a catheter assembly. The device includes an introducer body wherein the introducer body is comprised of an extension body with raised ribs on its surface and an enlarged portion with an attachment mechanism on its surface; and a collar which is used to mate with the introducer body; and wherein the extension body can be rotated within the collar.

In another exemplary embodiment, the present invention is a connecting assembly for a catheter system. The assembly includes an introducer body with an enlarged rectangularly shaped portion possessing an attachment mechanism on its surface; a collar capable of receiving and mating with the introducer body; an adhesive pad with a corresponding pad attachment mechanism used to form a reversible connection with the introducer body; and wherein the introducer body can be rotated within the collar in a circular manner.

In another exemplary embodiment, the present invention is a method for connecting a catheter assembly to a user. The method includes introducing a catheter having an introducer into an orifice of the user; pulling back the introducer; and attaching the introducer to a portion of the body of the user.

As used herein and throughout this disclosure, and in order to understand the directional aspects of this invention, "proximal" refers to the section of the device that is closer to the patient's body (e.g., urethra) during catheterization while "distal" refers to the section of the device that is farther away from the patient's body during catheterization.

DETAILED DESCRIPTION OF THE INVENTION

The present invention provides for catheter and catheter assemblies capable of mating with adhesive pads in order to increase a catheterized patient's mobility and prevent movement of the catheter in and out (pistoning) of the urethra. In particular embodiments and examples presented herein, such catheters are described with respect to urinary catheterization but it must be noted that such connection devices according to the present invention are not limited to urinary catheters alone but may be applicable to any catheter and catheter assembly that could benefit from the use of such connection devices.

Figure 1:
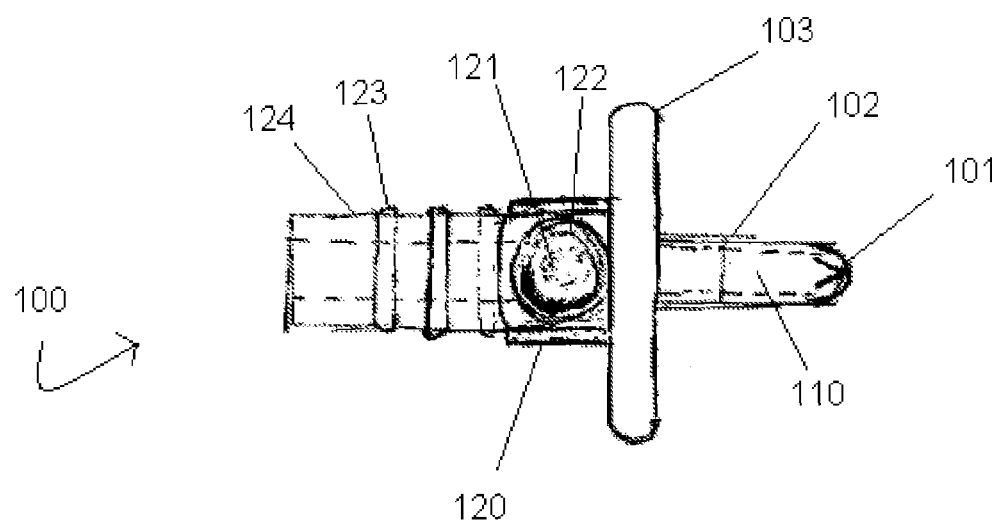
FIG. 1 shows a top view of a portion of a catheter assembly with an introducer wherein the introducer has an attachment mechanism on its surface capable of mating with a corresponding pad attachment mechanism according to an exemplary embodiment of the present invention.

An exemplary embodiment of the present invention incorporated into a catheter assembly 100 is shown in FIG. 1, and includes a guiding portion 102, flange 103, and an introducer body 120 with an attachment mechanism 121. The introducer body 120 may be rectangular in shape as shown in FIG. 1 or it may be of any other shape (e.g., oval, diamond, etc.) such that the body may be easily grasped and manipulated by the user. As such, the introducer body 120 may also be of a length and size such that it is capable of being easily grasped and manipulated. The introducer body 120 may also possess raised ribs 123 on its surface as shown in FIG. 1. These raised ribs 123 may act to prevent slippage during user manipulation of the introducer body 120, and they may also function to effectively mate with and provide frictional force against an inside surface of a collar (not shown in FIG. 1 but shown in FIG. 2).

The introducer body 120 may possess an attachment mechanism 121 on its surface just distal to the flange 103 wherein the attachment mechanism is capable of reversibly mating with a corresponding pad attachment mechanism (not shown). The attachment mechanism 121 may be circular as shown or it may be other shape (e.g., square, hexagonal, etc.) such that it may connect to and mate with a correspondingly shaped pad attachment mechanism (not shown). Additionally, the attachment mechanism 121 can be protrusive (e.g., with an external mating projection) instead of indented (e.g., with an internal receiving hole) as shown in FIG. 1. In the former case, the pad attachment mechanism would contain a corresponding receiving portion to mate with the protrusive portion. Still, the connection between the attachment mechanism 121 and the pad attachment mechanism may be reversibly formed so that the operator may connect and disconnect the attachment mechanism 121 whenever desired using a snapping or other reversibly securing action (e.g., snapping the pad attachment mechanism into the attachment mechanism 121 or vice versa). Once made, the connection is strong enough to avoid premature disconnection, and it is not too strong so as to prevent the user from disconnecting the assembly with reasonable force. Also, the connection between the attachment mechanism 121 and the pad attachment mechanism could be achieved through any other suitable reversible means including but not limited to hook and loop mechanism, such as, for example, VELCRO.

The guiding portion 102 should be of a diameter slightly larger than the diameter of a catheter 110 so that the catheter is able to freely and stably move through the length of the guiding portion 102. In this way, the user may grasp the introducer body 120 (which includes extension body 124) and the flange 103 while introducing the catheter 110 through aperture 101 and then into the patient's urethra. The aperture 101 may be created from a slitted "X" design as shown to form four flaps so the catheter is able to smoothly and stably slide through the assembly 100. The catheter 110 is able to slide within the guiding portion 102 as well as within the introducer body 120 and extension body 124. The introducer body 120, flange 103, and guiding portion 102 are able to rotate on the axis defined by the length of the catheter 110 in order to enable the user to easily align the attachment mechanism 121 with the pad attachment mechanism (not shown in FIG. 1) without having to rotate the entire catheter assembly. Thus, after the desired length of catheter 110 is positioned within the patient's urethra, the user may rotate the introducer body alone to locate the pad attachment mechanism on the adhesive pad. In order to maintain stable operability, the diameter of the catheter should fit snugly enough within the guiding portion 102 to prevent the introducer body 120 from rotating undesirably but not too snug so as to provide great resistance to the rotation of the introducer when so desired.

Figure 2:
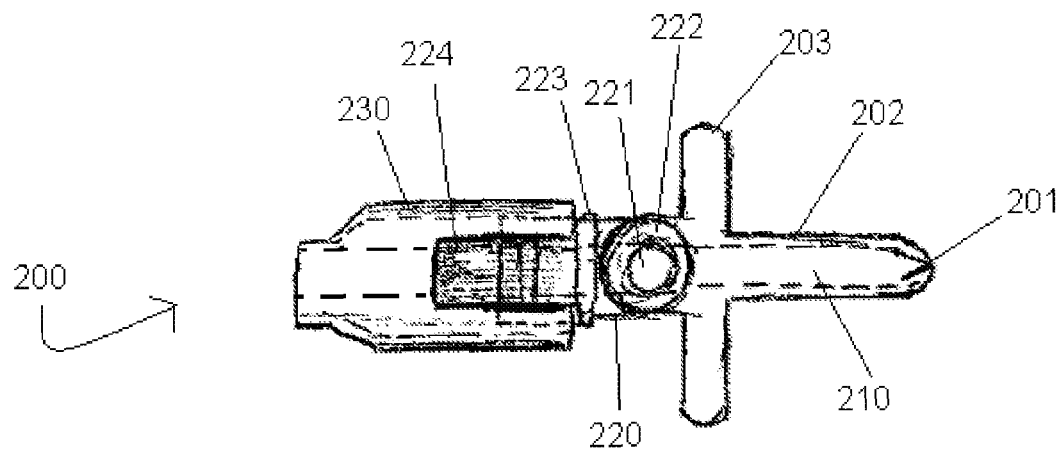
FIG. 2 shows a top view of a catheter assembly as shown in FIG. 1 with the distal end of the introducer mated with and situated within a collar according to an exemplary embodiment of the present invention.

Another exemplary embodiment of the present invention incorporated into a catheter assembly 200 is shown in FIG. 2, and includes a collar 230, a guiding portion 202, flange 203, and an introducer body 220 with an attachment mechanism 221 as described above with respect to FIG. 1. The collar 230 is of a slightly larger diameter than the diameter of the extension body 224 including the raised ribs 223 to allow the collar 230 to fit snugly around the extension body 124 as shown in FIG. 2. Once the extension body 224 is fitted deep enough into the collar 230 so as to prevent premature disconnection between the two objects, the operator is still able to rotate the introducer body 220 along with the flange 203 and guiding portion 202 within the collar 230. The raised ribs 223 function as a gripping surface for both the operator's hands (e.g., during connection of the collar 230 and the extension body 224) and for the interior surface of the collar 230 thereby providing some frictional force between the outer surface of extension body 224 and the inner surface of collar 230. This frictional force acts to keep the collar and introducer body combination fixed and stable, but may be overcome by the user when he or she desires to rotate the introducer body 220 in order to align the attachment mechanism 221 with a pad attachment mechanism (not shown). Thus, the raised ribs 223 are able to rotate within the collar 230 when a sufficient force is applied by the user.

The catheter 210 may extend through the extension body 224 and collar 230 as shown in FIG. 2. The catheter may continue past the collar 230 to be situated within a connecting tube (not shown) which then drains into a collection receptacle (not shown). The remaining portions of the labeled figure corresponding to those of FIG. 1 (e.g., the guiding portion 202, aperture 201, etc.) are subject to the same functional and structural limitations as described above.

Figure 3:
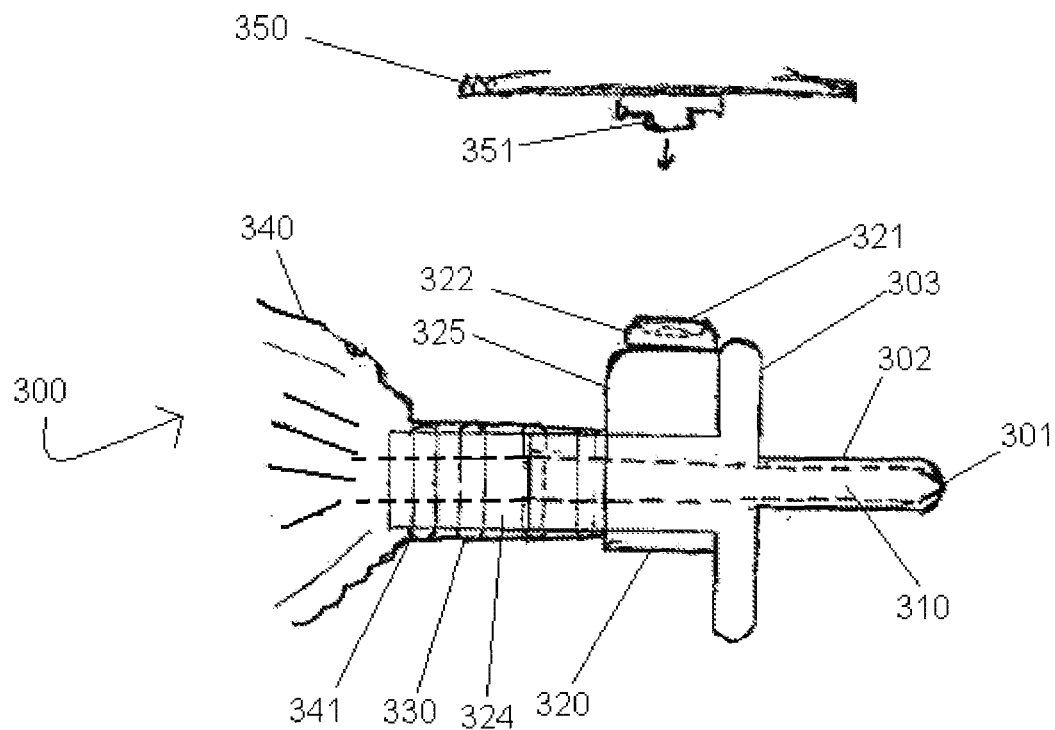
FIG. 3 shows a side view of a catheter assembly including an enlarged rectangularly shaped portion of an introducer being mated with a corresponding pad attachment mechanism on an adhesive pad according to an exemplary embodiment of the present invention.

Another exemplary embodiment of the present invention incorporated into a catheter assembly 300 is shown in FIG. 3, and includes a collar 330, a guiding portion 302, flange 303, a protecting body 340, an adhesive pad 350 with a pad attachment mechanism 351, and an introducer body 320 with an attachment mechanism 321 situated on the surface of an enlarged portion 325 of the introducer body. The enlarged portion 325 of the introducer body enables the user to more easily grasp and manipulate the introducer body as the body is translated along the axis of the catheter 310, and as the body is rotated after the desired length of catheter is inserted into the patient's urethra, for example. The enlarged portion of the introducer body allows the user more grasping area thereby enabling a more controlled manipulation of the introducer body. The enlarged portion is shown to be rectangular in FIG. 3, but it may be of any other shape so as to maximize operability and control of the body. Such shapes include but are not limited to a diamond and triangle. The enlarged shaped portion may also serve to facilitate connection with the pad attachment mechanism 351 as shown in FIG. 3. With the attachment mechanism 321 raised beyond the height of the flange 303, the operator has more vertical space with which to work during connection and can also stabilize the introducer body 320 during connection by grasping the enlarged portion around its sides.

The extension body 324 lays just distal to the enlarged portion 325 and resides within the collar 330 snugly enough to avoid premature disconnection as described above. The extension body 324 may also possess raised ribs on its surface as described above, and the collar 330 may possess raised ribs on its surface to enhance user manipulability and stability when the introducer body is translated or rotated. The diameters of the collar 330 and the extension body 324 are subject to the same parameters as described above (e.g., with the extension body 324 stably fitting within the collar 303 until disconnection is desired).

The protective body 340, which may be a sheath, may be connected to the collar 303 at attachment site 341 via any suitable means commonly used in the catheter arts including, but not limited to, heat sealing. The attachment site 341 and the means for forming it render the catheter assembly substantially impervious to harmful external bacteria. Thus, a leak-free seal is maintained at attachment site 341. The distal end of catheter 310 may also be situated within the protective body 340 as shown in FIG. 3. If the protective body 340 is a protective sheath, the sheath may be used to manipulate the catheter and keep it sterile. The protective body 340 may also be a connecting tube used as a fluid conduit for the drained fluid to pass into a collection receptacle (not shown). Alternatively, the protective body 340 may be a urine collection bag.

The adhesive pad 350 may be composed of any commonly used adhesive material known in the medical art so that the backside of the pad (e.g., the side opposite the pad attachment mechanism 351) can safely adhere to the skin of a patient. The pad attachment mechanism 351 may be composed of any commonly used material known in the medical art such that it is able to reversibly bind and mate with the attachment mechanism 321. This connection should be strong enough to avoid unwanted disconnection or unwanted rotation, and it should not be too strong so as to prevent disconnection when desired.

During connection between the adhesive pad 350 and the introducer body 320, the user may snap the pad attachment mechanism 351 into the attachment mechanism 321 as shown in FIG. 3. The size of the pad attachment mechanism 351 may be such that the protruding portion is able to effectively bind and mate with the attachment mechanism 321 to form a stable, yet reversible bond. The attachment ring 322 may make contact with the peripheral portion of the pad attachment mechanism 351 so that it provides frictional resistance to premature disconnection. The snapping attachment mechanism as described is not a limiting characteristic of this embodiment and the connection may be achieved via any other suitable means as described above (e.g., using hook and loop mechanisms, such as VELCRO). Once attached to the introducer body, the adhesive pad, which is adhering to a patient's thigh, for example, is able to effectively anchor the catheter assembly 300 to the patient's thigh thereby allowing for increase patient mobility.

The remaining portions of the labeled figure corresponding to those of FIG. 1 (e.g., the guiding portion 302, aperture 301, etc.) are subject to the same functional and structural limitations as described above.

Figure 4:
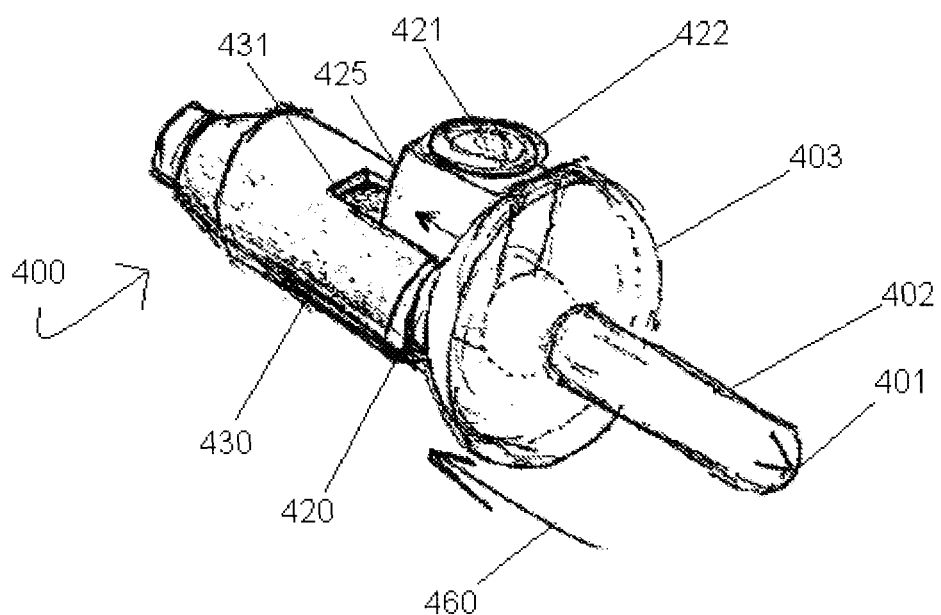
FIG. 4 shows an angled front view of a catheter assembly including an enlarged rectangularly shaped portion of an introducer being mated with a collar possessing a receiving space according to an exemplary embodiment of the present invention.

Another exemplary embodiment of the present invention incorporated into a catheter assembly 400 is shown in FIG. 4, and includes a flange 403, introducer body 420 with an enlarged portion 425, attachment mechanism 421, and a collar 430 with a receiving aperture 431. The receiving aperture 431 provides a mechanism for connecting the enlarged portion 425 with the collar 430. Once the desired length of catheter is inserted, the user may connect the introducer body 420 with the collar 430 via the receiving aperture 431. This connection allows the user to more stably lock into place the introducer body. The receiving aperture 431 may be rectangularly shaped as shown in FIG. 4, or it may be of any other shape (e.g., triangular, diamond-shaped, etc.) such that it is able to effectively mate with a correspondingly shaped enlarged portion 425.

The user exerts force in the direction of arrow 460 in order to lock the introducer body 420 within the collar 430. Since the enlarged portion 425 may range in shape, the receiving aperture 431 may range in shape as well, as long as it is correspondingly shaped to receive the enlarged portion 425 and to form a stable connection. The receiving aperture 431 is deep enough to receive the enlarged portion 425, and once connected, the entire enlarged portion 425 may be situated within the receiving aperture 431 and the distal surface of the flange 403 may make contact with the proximal surface of the collar 430. After the connection is made between the collar and the introducer body, the collar 430 may or may not be rotated along with the introducer body 420 in order to align the attachment mechanism 421 with the pad attachment mechanism (not shown). If the collar 430 is able to be rotated, then it should be attached to assembly 400 such that it does not freely rotate on its own, but requires sufficient external user force to do so. Thus, the diameters and contacting surfaces of the collar 430 and the introducer body 420 should be such that the introducer body can be stably situated within the collar 430. The introducer body may also have an extension body (as described above but not shown), which is used to make the contact with the inner surface of the collar to prevent premature rotation of the assembly. The ability of the collar 430 to rotate along with the introducer body 420 allows the user a larger surface area to grasp.

The receiving aperture 431 may be located anywhere along the proximal surface of the collar so that after the introducer body is rotated to align the attachment mechanism with the pad attachment mechanism (not shown in FIG. 4), the user may lock the introducer body into place with the collar thereby avoiding undesired rotational movement of the introducer body 420. The collar 430 may or may not be rotatable and its receiving aperture would function as a stabilizing mechanism in either instance to keep the introducer body with its attachment mechanism pointing downward, for example (e.g., rotated 180 degrees counter-clockwise from the position shown in FIG. 4). If the collar is rotatable, the collar must be of a diameter and size so as to prevent undesired rotation. In other words, the collar may not be able to rotate on its own freely, and it must be able to rotate only to a desired position and no further.

The remaining portions of the labeled figure corresponding to those of FIG. 1 (e.g., the guiding portion 402, aperture 401, etc.) are subject to the same functional and structural limitations as described above.

Figure 5:
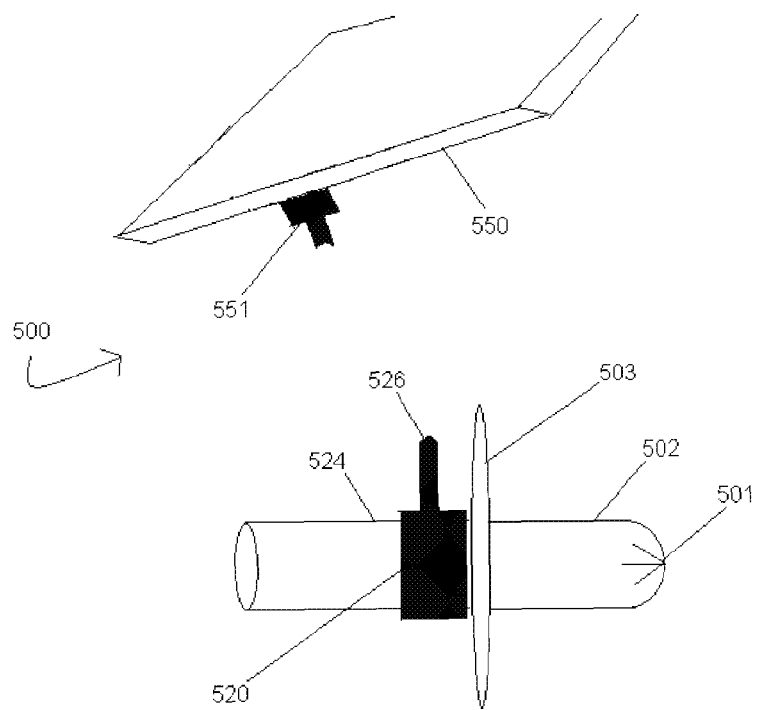
FIG. 5 shows a side view of a catheter assembly including an introducer with an attachment mechanism situated just distal to a flange wherein the attachment mechanism is capable of being mated with a corresponding pad attachment mechanism on an adhesive pad according to an exemplary embodiment of the present invention.
Figure 6:
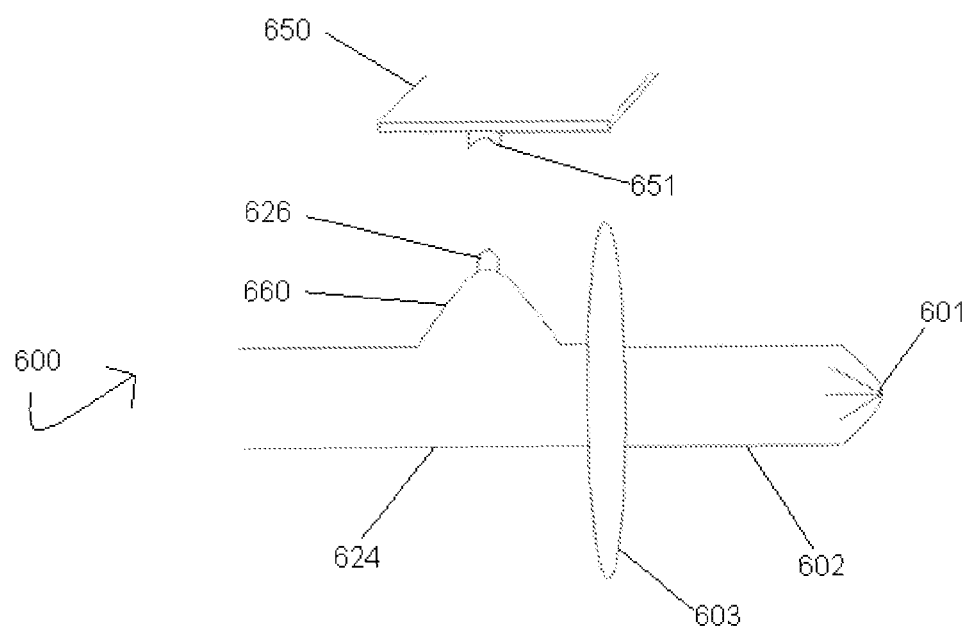
FIG. 6 shows a side view of a catheter assembly including an enlarged triangularly shaped portion of an introducer with an attachment mechanism on the introducer's surface capable of being mated with a corresponding pad attachment mechanism on an adhesive pad according to an exemplary embodiment of the present invention.

Another exemplary embodiment of the present invention incorporated into catheter assembly 500 is shown in FIG. 5, and includes a flange 503, attachment mechanism 520 with a mating piece 526, and an adhesive pad 550 with a pad attachment mechanism 551. The attachment mechanism 520 may be situated just distal to the flange 503 and may encompass the diameter of the extension body 524 as shown in FIG. 5. The attachment mechanism 520 may be able to rotate independently or along with the flange and guiding portion in a circular fashion to align the mating piece 526 with the pad attachment mechanism 551. In essence, the attachment mechanism 520 acts as a circular "collar" that may be slid over the introducer body and has an ability to mate with a pad. If it is able to rotate, the attachment mechanism is stably bound to the extension body 524 such that it does not freely rotate without external force. Such a connection may be achieved by, but is not limited to, the presence of raised ribs on the inner surface of the attachment mechanism 520 that are capable of applying some frictional resistance to rotation of the mechanism which may be overcome by sufficient user force.

The mating piece 526 may fitted into the pad attachment mechanism 551 via a snapping action so as to form a stable yet reversible connection. Such a connection is not limited to a snapping action and may be achieved through any of the aforementioned means (e.g., hook and loop mechanisms, such as VELCRO). Once the connection is achieved, the adhesive pad is able to effectively anchor the catheter assembly 500 in place on the patient's leg.

The remaining portions of the labeled figure corresponding to those of FIG. 1 (e.g., the guiding portion 502, aperture 501, etc.) are subject to the same functional and structural limitations as described above.

Another exemplary embodiment of the present invention is incorporated into catheter assembly 600 and includes a flange 603, guiding portion 602, raised mating surface 660 with attachment mechanism 626, and an adhesive pad 650 with a pad attachment mechanism 651. The raised mating surface 660 may be attached to the extension body 624 located just distal to the flange 603 as shown or it may be an independent mechanism similar the attachment mechanism and mating piece shown in FIG. 5. In either case, the raised mating surface 660 may increase operator dexterity when aligning the attachment mechanism 626 with the pad attachment mechanism 651. The raised mating surface may also increase operator manipulability when rotating the raised mating surface 660 around the horizontal axis formed by the extension body 624 and the guiding portion 602 (e.g., rotating the raised mating surface in a circular manner). Similar to that described above, a collar (not shown) may encompass the portion of the extension body 624 just distal to the raised mating surface 660, and it would be of such a diameter so as to snugly fit around the extension body but still allow rotational movement of the body as described.

The connection between the attachment mechanism 626 and the pad attachment mechanism 651 may be formed via a snapping action. Such an action though is not limiting and other mechanisms can be used to achieve the connection (e.g., hook and loop mechanisms, such as VELCRO) as long as the connection is strong enough to avoid undesired rotational movement, but not so strong so as to prevent desired rotational movement or slippage. The raised mating surface 660 also makes it easier for the connection to be made with the pad attachment mechanism since the attachment mechanism 626 is raised above the surface of the extension body 624 thereby providing a protrusive surface for the operator to grasp and manipulate during connection.

The remaining portions of the labeled figure corresponding to those of FIG. 1 (e.g., the guiding portion 602, aperture 601, etc.) are subject to the same functional and structural limitations as described above.

Unless otherwise specified, all of the materials used for the present invention may be comprised of artificial or naturally occurring non-degradable biocompatible polymer or rubber compounds such that the materials used for the present invention serve the functions delineated in this application. Such compounds can include, but are not limited to, polyester based biocompatible polymers, nylon-based biocompatible polymers, latex based biocompatible polymers, Teflon, polytetrafluoroethylene (PTFE) polymers, polyvinyl chloride (PVC) polymers, silicone polymers, polyurethane polymers, silicone polyurethane polymers, ethylene-vinyl acetate copolymers, polyethylene polymers, and thermoplastic polymers.

The manufacturing methods that can be employed for the present invention include, but are not limited to, conventional techniques used in the industry to produce similar function products, as apparent to one having ordinary skill in the art.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. An assembly for securing a catheter device to a user, the assembly comprising:
   an introducer body surrounding the catheter device;
   a catheter attachment mechanism exterior to the introducer body, the catheter attachment mechanism capable of reversibly mating with a corresponding pad attachment mechanism;
   a collar adapted to mate with an extension body;
   the extension body at a distal end of the introducer body, the extension body having raised ribs to allow the collar to fit around the extension body;
   and wherein the catheter attachment mechanism may rotate about an axis defined by the length of the catheter device in order to align with the pad attachment mechanism.

2. The assembly of claim 1, wherein the introducer body rotates about the axis with the catheter attachment mechanism.

3. The assembly of claim 1, wherein the catheter attachment mechanism acts as said collar and may rotate freely around the extension body.

4. The assembly of claim 1, wherein the catheter device is a urinary catheter.

5. The assembly of claim 1, wherein the catheter attachment mechanism is one of a circular, square, and hexagonal shape such that the catheter attachment mechanism may connect to and mate with a correspondingly shaped pad attachment mechanism.

6. The assembly of claim 1, wherein the catheter attachment mechanism is an external mating projection on the introducer body.

7. The assembly of claim 1, wherein the catheter attachment mechanism is an internal receiving hole in the introducer body.

8. The assembly of claim 1, wherein the catheter attachment mechanism is a hook and loop mechanism.

9. The assembly of claim 1, wherein the introducer body further comprises a guiding portion, the guiding portion slightly larger than the diameter of the catheter device.

10. The assembly of claim 1, further comprising a protective body.

11. The assembly of claim 10, wherein the protective body is a protective sheath which may be used to manipulate the catheter device and keep the catheter device sterile.

12. A system for urinary catheterization, the system comprising:
 a catheter device including an introducer body surrounding the catheter device, and a catheter attachment mechanism coupled to the introducer body; and
 an adhesive pad having a pad attachment mechanism, the pad attachment mechanism capable of reversibly mating with the catheter attachment mechanism, the adhesive pad having an adhesive material to adhere to a patient;
 an enlarged portion of the introducer body containing the catheter attachment mechanism;
 a collar with a receiving aperture, the receiving aperture providing a mechanism for connecting the enlarged portion with the collar to lock the introducer body into place;
 wherein the catheter attachment mechanism may rotate about an axis defined by the length of the catheter device in order to align with the pad attachment mechanism.

13. The system of claim 12, further comprising a protective body connected to the collar.

* * * * *